United States Patent
Chou et al.

(10) Patent No.: US 10,086,164 B2
(45) Date of Patent: Oct. 2, 2018

(54) MEDICAL JOINT AND CHECK VALVE MODULE THEREOF

(71) Applicants: Jeng-Yu Chou, Yilan County (TW); Jiunn-Rong Chen, Taichung (TW)

(72) Inventors: Jeng-Yu Chou, Yilan County (TW); Shi-Chuan Chang, Yilan County (TW); Chin-Wei Chen, Yilan County (TW)

(73) Assignees: Jeng-Yu Chou, Yilan County (TW); Jiunn-Rong Chen, Taichung (TW)

( * ) Notice: Subject to any disclaimer, the term of this patent is extended or adjusted under 35 U.S.C. 154(b) by 513 days.

(21) Appl. No.: 14/847,866

(22) Filed: Sep. 8, 2015

(65) Prior Publication Data
US 2017/0065788 A1  Mar. 9, 2017

(51) Int. Cl.
| | |
|---|---|
| *A62B 18/10* | (2006.01) |
| *A62B 9/02* | (2006.01) |
| *A62B 9/06* | (2006.01) |
| *A61M 16/08* | (2006.01) |
| *A61M 16/20* | (2006.01) |

(Continued)

(52) U.S. Cl.
CPC ....... *A61M 16/0833* (2014.02); *A61M 15/009* (2013.01); *A61M 16/0463* (2013.01); *A61M 16/208* (2013.01)

(58) Field of Classification Search
CPC .... A61M 6/0833; A61M 39/00; A61M 39/22; A61M 16/0833; A61M 16/0816; A61M 16/0875; A61M 16/0883; A61H 2005/3128

See application file for complete search history.

(56) References Cited

U.S. PATENT DOCUMENTS

| | | | | |
|---|---|---|---|---|
| 4,655,752 A | * | 4/1987 | Honkanen | A61M 39/06 604/167.02 |
| 5,176,652 A | * | 1/1993 | Littrell | A61M 39/0606 137/849 |

(Continued)

FOREIGN PATENT DOCUMENTS

| | | |
|---|---|---|
| EP | 1269925 A1 | 1/2003 |
| EP | 2604203 A1 | 6/2013 |

OTHER PUBLICATIONS

Search Report dated Dec. 10, 2015 of the Corresponding European Patent Application No. 15184923.9.

*Primary Examiner* — Nyca T Nguyen
(74) *Attorney, Agent, or Firm* — Chun-Ming Shih; HDLS IPR Services (57) ABSTRACT

A medical joint and a check valve module thereof are used in a connection tube having a communicating opening. The check valve module includes a first membrane and a second membrane. The first membrane is assembled to the communicating opening to seal the same. The first membrane includes a first slit. The first membrane and the second membrane are disposed overlappingly. The second membrane includes a second slit. Accordingly, it facilitates inserting a detector into the connection tube to detect gas pressure, MDI, gas, temperature, or inserting a suction tube to remove sputum, and prevents the gas inside the connection tube from leaking out from an intersection of a first slit and a second slit, thereby achieving handiness and a gas-leak-proof effect of the medical joint and the check valve module.

18 Claims, 6 Drawing Sheets

(51) Int. Cl.
*A61M 15/00* (2006.01)
*A61M 16/04* (2006.01)

(56) References Cited

U.S. PATENT DOCUMENTS

| | | | | |
|---|---|---|---|---|
| 5,603,702 | A * | 2/1997 | Smith | A61B 17/3462 251/149.1 |
| 5,613,954 | A * | 3/1997 | Nelson | A61B 17/3421 604/167.03 |
| 5,779,697 | A * | 7/1998 | Glowa | A61B 17/3462 606/185 |
| 5,993,471 | A * | 11/1999 | Riza | A61B 17/3498 606/185 |
| 6,296,624 | B1 * | 10/2001 | Gerber | A61B 10/0045 604/164.09 |
| 6,551,282 | B1 * | 4/2003 | Exline | A61B 17/3462 604/167.01 |
| 6,551,283 | B1 * | 4/2003 | Guo | A61M 39/06 251/149.1 |
| 7,798,991 | B2 * | 9/2010 | Insignares | A61B 17/3498 604/165.01 |
| 7,850,653 | B2 * | 12/2010 | Hammond | A61B 17/3462 251/149.3 |
| 7,931,624 | B2 * | 4/2011 | Smith | A61B 1/00154 604/167.06 |
| 7,938,804 | B2 * | 5/2011 | Fischvogt | A61B 17/3462 604/167.01 |
| 8,137,321 | B2 * | 3/2012 | Argentine | A61M 25/0097 604/167.06 |
| 8,430,812 | B2 * | 4/2013 | Barnes | A61B 17/3462 600/205 |
| 9,089,363 | B2 * | 7/2015 | Dooney, Jr. | A61B 17/3421 |
| 2003/0181858 | A1 * | 9/2003 | Lajtai | A61B 17/3421 604/167.06 |
| 2004/0073176 | A1 * | 4/2004 | Utterberg | A61M 39/02 604/256 |
| 2004/0221851 | A1 * | 11/2004 | Madsen | A61M 16/0463 128/207.14 |
| 2004/0230161 | A1 * | 11/2004 | Zeiner | A61B 17/34 604/167.06 |
| 2005/0161048 | A1 | 7/2005 | Rapacki | |
| 2009/0076464 | A1 * | 3/2009 | Gresham | A61B 17/3498 604/264 |
| 2010/0024818 | A1 | 2/2010 | Stenzler | |
| 2012/0089160 | A1 * | 4/2012 | Lunn | A61B 17/3462 606/148 |
| 2013/0150792 | A1 * | 6/2013 | Alonso | A61B 17/3417 604/167.01 |

* cited by examiner

MEDICAL JOINT AND CHECK VALVE MODULE THEREOF

TECHNICAL FIELD

The present invention relates to a medical joint and, in particular, to a medical joint and a check valve module.

BACKGROUND

A medical joint is extensively used in medical institutions and medical treatment. For example, if a patient does not breathe spontaneously, a mechanical ventilator is often used to assist in breath. The mechanical ventilator includes a breathing tube, and the medical joint is assembled between the breathing tube and a breathing mask on the patient's face. The medical joint communicates with the breathing tube and the breathing mask for delivering a gas generated by the mechanical ventilator to the breathing mask.

The present medical joint is often integrally formed with an extension tube extending therefrom. The extension tube is configured for insertion of a detector for detecting gas pressure, MDI, gas, and temperature, for insertion of a suction tube for removing sputum, or for other effects. However, the medical joint tends to have a problem of leaking an internal gas out from the extension tube of the medical joint, thereby affecting the gas pressure or concentration, or even worse, compromising the medical treatment to patient.

In view of the foregoing, the inventor made various studies to improve the above-mentioned problems, on the basis of which the present invention is accomplished.

SUMMARY

It is an object of the present invention to provide a medical joint and a check valve module, wherein a first slit and a second slit intersect each other so as to facilitate inserting a detector into the connection tube, via an intersection of the first slit and the second slit, to detect gas pressure, MDI, gas, temperature, or to facilitate inserting a suction tube for removing sputum, and to prevent the gas inside the connection tube from leaking out from the intersection of the first slit and the second slit, so as to achieve handiness and a gas-leak-proof effect of the medical joint and the check valve module.

Accordingly, the present invention provides a medical joint. The medical joint comprises: a connection tube, the connection tube including a first tube and a second tube extending from and communicating with the first tube, two ends of the first tube including a communicating opening and a first junction respectively, a distal end of the second tube including a second junction; and a check valve module, the check valve module being assembled to the communicating opening to seal the same, the check valve module including a first membrane and a second membrane disposed overlappingly, the first membrane including a first slit, the second membrane including a second slit, the first slit and the second slit intersecting each other.

Accordingly, the present invention provides a check valve module for use with a connection tube. The connection tube includes a communicating opening. The check valve module comprises: a first membrane, the first membrane being assembled to the communicating opening to seal the same, the first membrane including a first slit; and a second membrane, the first membrane and the second membrane being disposed overlappingly, the second membrane including a second slit, the first slit and the second slit intersecting each other.

The present invention further has the following effects:

First, the medical joint further includes a first rotatable tube and a second rotatable tube, the first rotatable tube is connected to the first junction and rotatable with respect to the first tube, and the second rotatable tube is connected to the second junction and rotatable with respect to the second tube. Therefore, when the first rotatable tube or the second rotatable tube is connected to other external tubing, the position of the connection tube is maintained even if inadvertently touching, moving or rotating the external tubing, thereby enhancing the safety in using the medical joint.

Second, the first plate and the second plate are each a convex plate protruding in a direction away from the communicating opening, so that the first slit and the second slit are opened toward the same direction as the inserting direction of the detector or the suction tube, thereby guiding the detector or the suction tube to be inserted into the communicating opening, so as to promote convenience in using the medical joint and the check valve module.

BRIEF DESCRIPTION OF THE DRAWINGS

The disclosure will become more fully understood from the detailed description and the drawings given herein below for illustration only, and thus does not limit the disclosure, wherein.

DETAILED DESCRIPTION

Detailed descriptions and technical contents of the present invention are illustrated below in conjunction with the accompany drawings. However, it is to be understood that the descriptions and the accompany drawings disclosed herein are merely illustrative and exemplary and not intended to limit the scope of the present invention.

Referring to FIGS. 1 to 5, the present invention provides a medical joint and a check valve module thereof. The medical joint 10 includes a connection tube 1 and a check valve module 2. The check valve module 2 includes a first membrane 21 and a second membrane 22.

Figure 1:
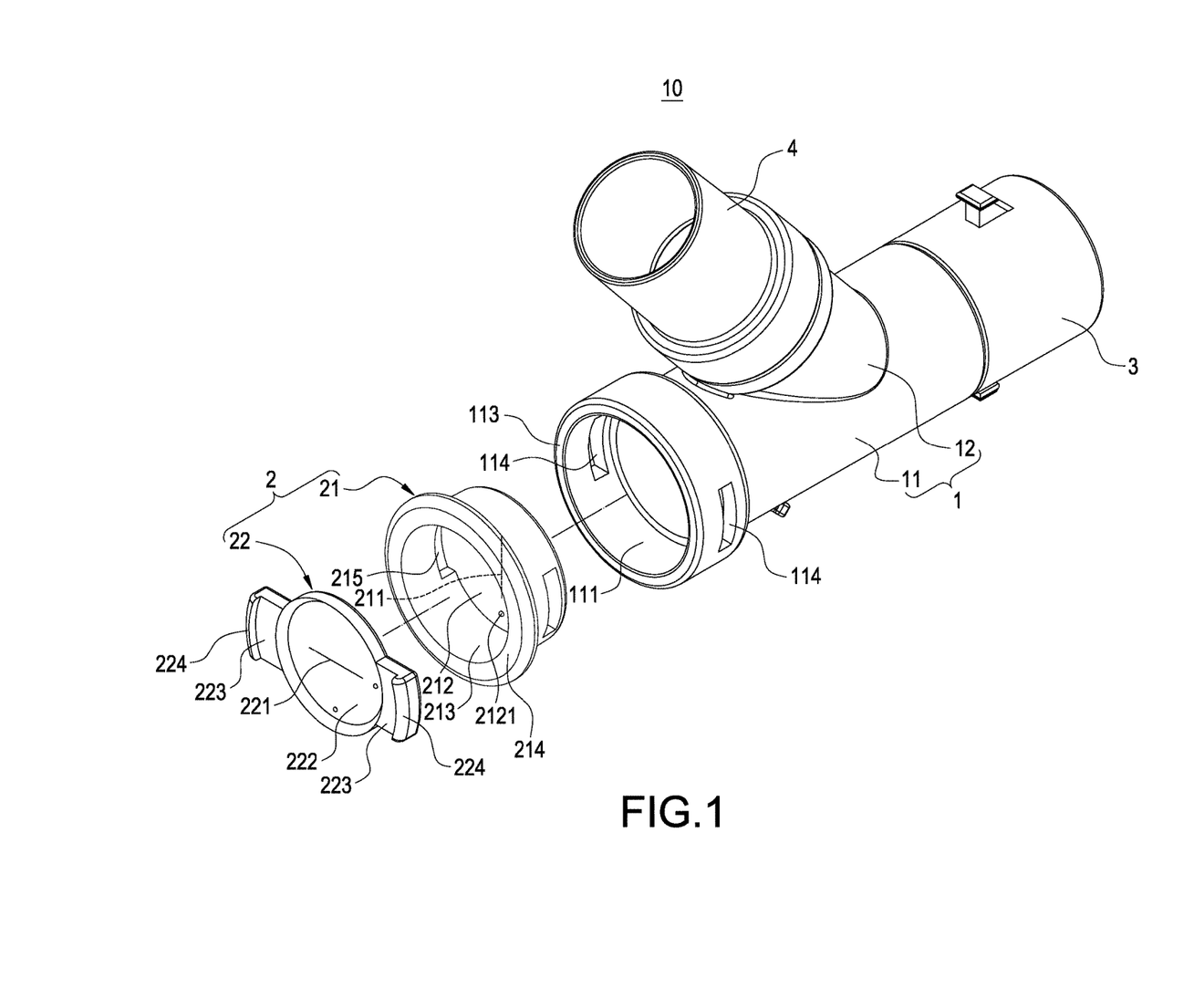
FIG. 1 is a perspective exploded view of a medical joint according to the present invention.
Figure 2:
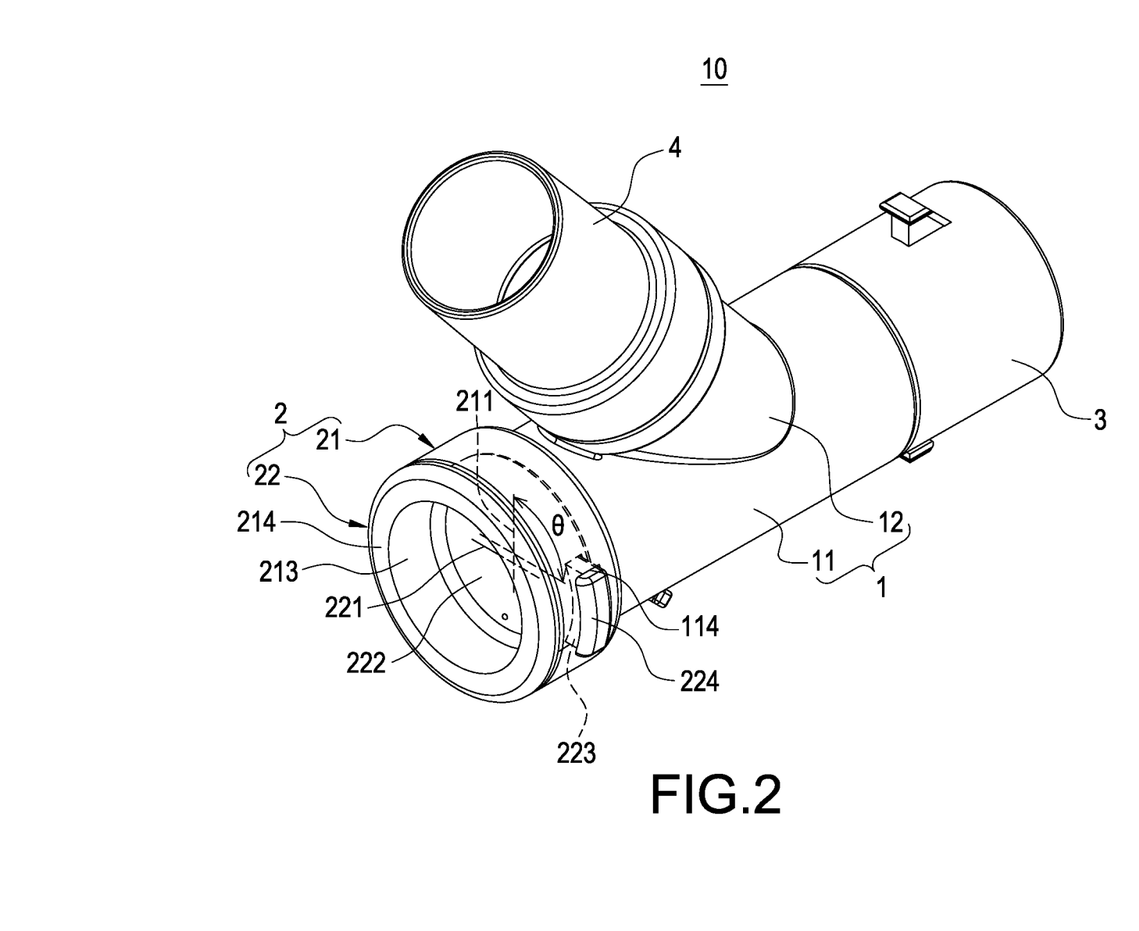
FIG. 2 is a perspective assembled view of the medical joint according to the present invention.

The connection tube 1 can be linear, Y-shaped, T-shaped, or of other suitable shape. In the present embodiment, the connection tube 1 is a Y-shaped tube as an example; however, the present invention is not limited thereto.

Referring to FIGS. 1 to 4, the connection tube 1 includes a first tube 11 and a second tube 12 extending from and communicating with the first tube 11. Two ends of the first tube 11 include a communicating opening 111 and a first junction 112 respectively. A distal end of the second tube 12 includes a second junction 121. An included angle θ is formed between the first slit 211 and the second slit 221, and the included angle θ ranges from 30 to 150 degrees. In the best embodiment, the included angle θ is 90 degrees.

The first tube 11 forms a rim 113 at the communicating opening 111. A wall of the first tube 11 is disposed with two vents 114 opposite to each other. A first engagement ring 115 extends from an inner wall surface of the first tube 11.

Referring to FIGS. 1 to 4, the check valve module 2 is assembled to the communicating opening 111 to seal the same. The check valve module 2 includes a first membrane 21 and a second membrane 22 disposed overlappingly. The first membrane 21 includes a first slit 211, the second membrane 22 includes a second slit 221, and the first slit 211 and the second slit 221 intersect each other.

In detail, the first membrane 21 includes a first plate 212 and an annular wall 213 extending from a periphery of the first plate 212. The annular wall 213 forms a stop ring 214 extending outwardly from one end of the annular wall 213 disposed away from the first plate 212. The annular wall 213 is disposed with two through holes 215 opposite to each other. The first slit 211 is formed on the first plate 212. The annular wall 213 is inserted in the first tube 11 and contacts the same. The stop ring 214 and the rim 113 abut each other for securement therebetween.

The second membrane 22 has a second plate 222 and two wings 223 extending from two sides of the second plate 222, a protrusion 224 extends from a distal end of each of the wings 223, the second slit 221 is formed on the second plate 222, the second plate 222 and the first plate 212 overlap and contact each other, the wings 223 pass through the respective through holes 215 and the respective vents 114 for securement, and the protrusion 224 and the first tube 11 engage each other.

Figure 3:
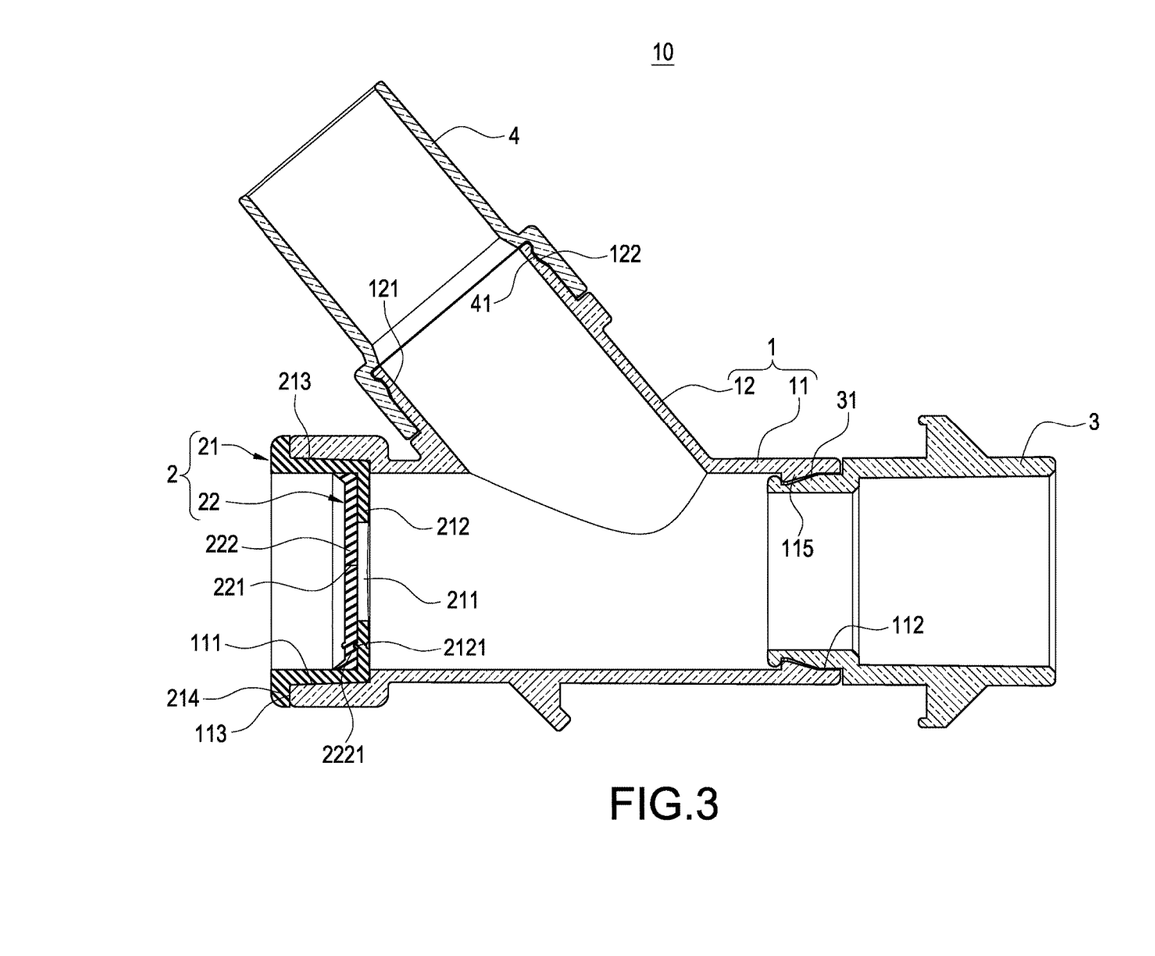
FIG. 3 is a cross-sectional view of the medical joint according to the present invention.
Figure 4:
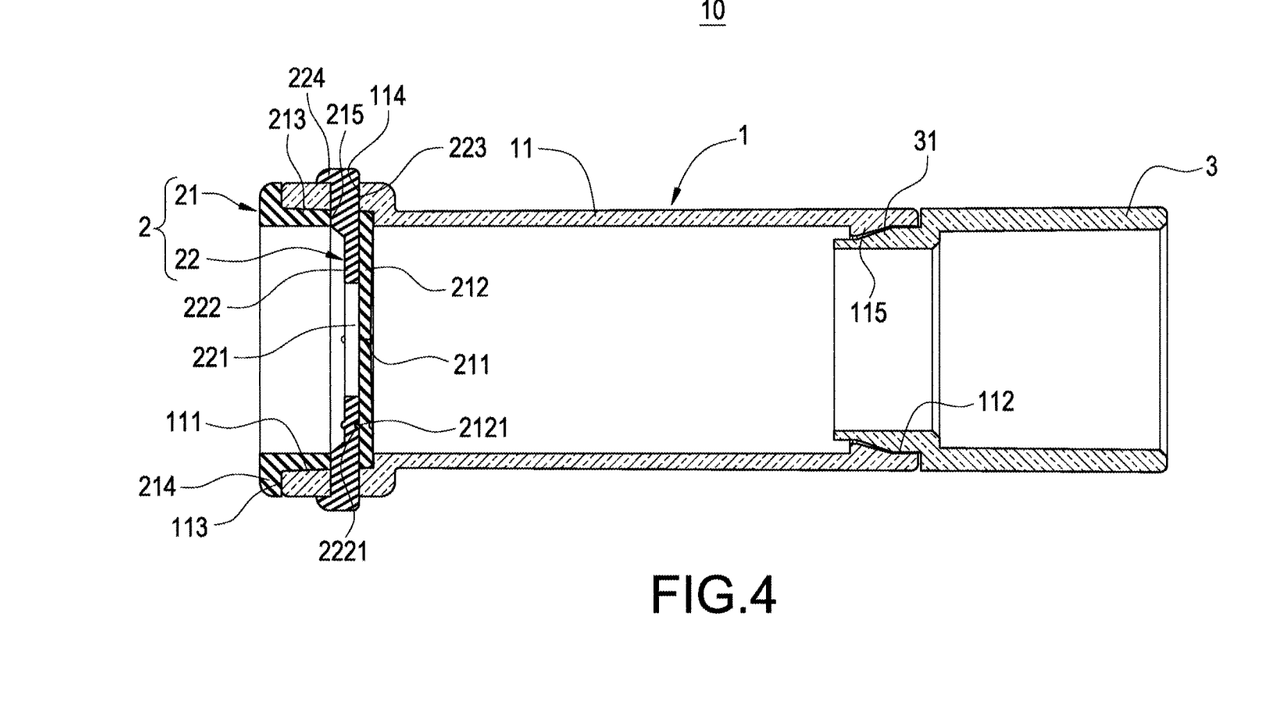
FIG. 4 is another cross-sectional view of the medical joint according to the present invention.

Furthermore, as shown in FIGS. 3 and 4, the first plate 212 includes a plurality of protruding points 2121 extending therefrom, the second plate 222 is disposed with a plurality of trenches 2221, the protruding points 2121 are engaged with the trenches 2221 respectively, thereby preventing the first plate 212 from moving or rotating with respect to the second plate 222, so as to secure the first plate 212 in position.

Referring to FIGS. 1 to 4, the medical joint 10 further comprises a first rotatable tube 3 and a second rotatable tube 4, the first rotatable tube 3 is connected to the first junction 112 and rotatable with respect to the first tube 11, and the second rotatable tube 4 is connected to the second junction 121 and rotatable with respect to the second tube 12.

In detail, a first annular recess 31 is formed on the exterior of the first rotatable tube 3, the first rotatable tube 3 is inserted in the first tube 11 via the first junction 112, the first engagement ring 115 is engaged with the first annular recess 31, and thereby the first rotatable tube 3 is rotatable with respect to the first tube 11.

A second annular recess 122 is formed on the exterior of the second tube 12, a first engagement ring 41 extends from the interior of the second rotatable tube 4, one end of the second rotatable tube 4 encloses the second junction 121 of the second tube 12, and the first engagement ring 41 is engaged with the second annular recess 122, and thereby the second rotatable tube 4 is rotatable with respect to the second tube 12.

Moreover, the first membrane 21 and the second membrane 22 consist of plastic, rubber, or other suitable materials. The first tube 11, the second tube 12, the first membrane 21, the second membrane 22, the first rotatable tube, or the second rotatable tube 4 can consist of or can be coated by an antibacterial material such as a silver-iron antibacterial material, so that the first tube 11, the second tube 12, the first membrane 21, the second membrane 22, the first rotatable tube 3, or the second rotatable tube 4 have an antibacterial property.

Referring to FIGS. 3 and 4, the medical joint 10 of the present invention includes a connection tube 1 and the check valve module 2. The connection tube 1 includes a first tube 11 and a second tube 12 extending from and communicating with the first tube 11, two ends of the first tube 11 includes a communicating opening 111 and a first junction 112 respectively, and a distal end of the second tube 12 includes a second junction 121. The check valve module 2 is assembled to the communicating opening 111 to seal the same, the check valve module 2 includes a first membrane 21 and a second membrane 22 disposed overlappingly, the first membrane 21 includes a first slit 211, the second membrane 22 includes a second slit 221, and the first slit 211 and the second slit 221 intersect each other.

Referring to FIGS. 3 and 4, in the check valve module 2, the first membrane 21 and the second membrane 22 are disposed overlappingly, the second membrane 22 includes a second slit 221, and the first slit 211 and the second slit 221 intersect each other.

Figure 5:
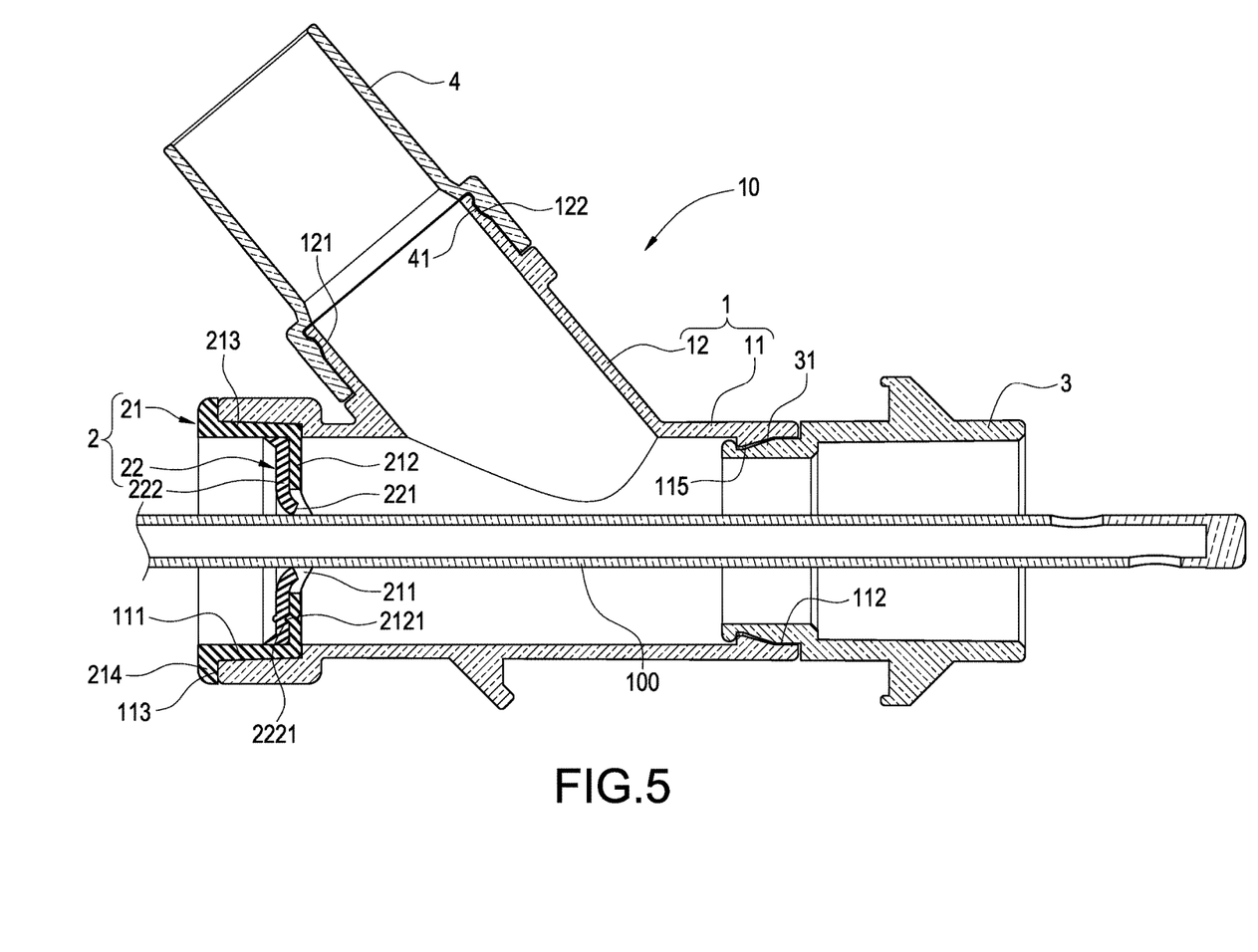
FIG. 5 is a schematic view showing a use state of the medical joint according to the present invention.

Referring to FIG. 5 which illustrates a use state of the medical joint 10 and the check valve module 2, the first membrane 21 is opened or closed via the first slit 211, and the second membrane 22 is opened or closed via the second slit 221, thereby facilitating inserting a detector into the connection tube 1 via an intersection of the first slit 211 and the second slit 221 so as to detect gas pressure, MDI, gas, temperature, or inserting a suction tube 100 to remove sputum. The first slit 211 and the second slit 221 intersect each other, so interference occurs between the open first membrane 21 and the open second membrane 22, thereby preventing the first membrane 21 and the second membrane 22 from opening too widely, thus avoiding a gas inside the connection tube 1 from leaking out from the intersection of the first slit 211 and the second slit 221, consequently achieving convenience and a gas-leak-proof property in using the medical joint 10 and the check valve module 2.

Referring to FIGS. 1 to 5, the annular wall 213 is inserted in the first tube 11 and contacts the same, the stop ring 214 and the rim 113 abut each other for securement therebetween, the second plate 222 and the first plate 212 overlap and contact each other, the wings 223 pass through the respective through holes 215 and the respective vents 114 for securement, and the protrusion 224 and the first tube 11 engage each other, so that the first membrane 21 and the second membrane 22 are assembled securely to seal the communicating opening 111. Furthermore, the protruding points 2121 are engaged with the trenches 2221 respectively, thereby preventing the first plate 212 from moving or rotating with respect to the second plate 222, thus enhancing securement between the first membrane 21 and the second membrane 22.

Furthermore, referring to FIGS. 1 to 5, the medical joint 10 further includes a first rotatable tube 3 and a second rotatable tube 4, the first rotatable tube 3 is connected to the first junction 112 and rotatable with respect to the first tube 11, and the second rotatable tube 4 is connected to the second junction 121 and rotatable with respect to the second tube 12. Therefore, when the first rotatable tube 3 or the second rotatable tube 4 is connected to other external tubing, the position of the connection tube 1 is maintained even if inadvertently touching, moving or rotating the external tubing, thereby enhancing the safety in using the medical joint 10.

Figure 6:
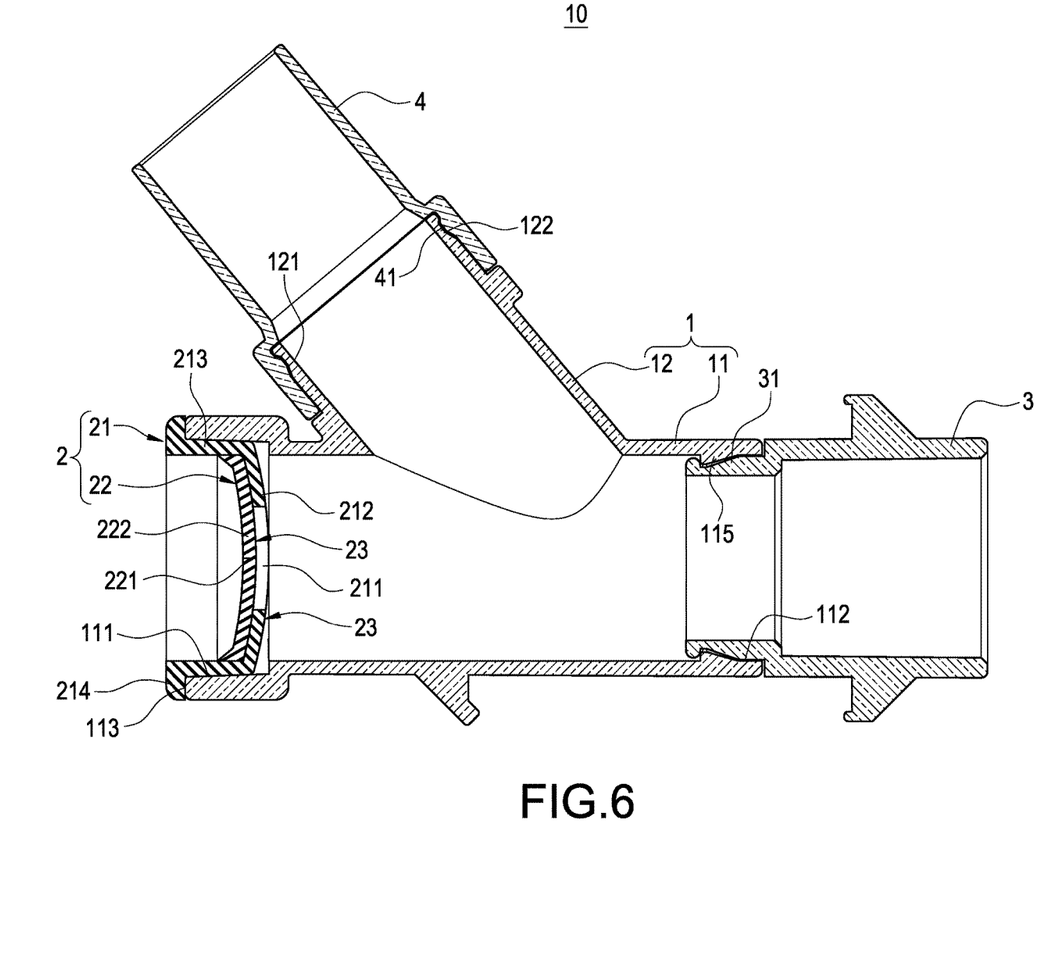
FIG. 6 is another cross-sectional view of the medical joint according to another embodiment of the present invention.

FIG. 6 illustrates the medical joint and the check valve module 2 according to another embodiment of the present invention. The embodiment in FIG. 6 is similar to the embodiment in FIGS. 1 to 5. The embodiment shown in FIG. 6 is different from the embodiment shown in FIGS. 1 to 5 in that the first plate 212 and the second plate 222 are each a convex plate 23 protruding in a direction away from the communicating opening 111.

In detail, the first plate 212 and the second plate 222 are each a convex plate 23 protruding in a direction away from the communicating opening 111, so when the detector or the suction tube is inserted into the connection tube 1 via the communicating opening 111, the first slit 211 and the second slit 221 are opened toward the same direction as the inserting direction of the detector or the suction tube, thereby guiding the detector or the suction tube to be readily inserted into the communicating opening, so as to promote convenience in using the medical joint 10 and the check valve module 2.

Each convex plate 23 can be a plano-convex plate or a concavo-convex plate. In the present embodiment, each convex plate 23 is a concavo-convex plate; however, the present invention is not limited thereto.

In summary, the medical joint and the check valve module according to the present invention is neither seen nor used in public. The present invention also possesses utility, novelty and non-obviousness requirements as set forth in the patent law. Therefore, a grant of letters patent for the present invention is respectively requested to protect the rights of the inventor.

What is claimed is:

1. A medical joint, comprising:
   a connection tube including a first tube and a second tube extending from and communicating with the first tube, two ends of the first tube including a communicating opening and a first junction respectively, a distal end of the second tube including a second junction; and
   a check valve module assembled to the communicating opening to seal the communicating opening, the check valve module including a first membrane and a second membrane disposed overlappingly, the first membrane including a first slit, the second membrane including a second slit,
   wherein the first tube forms a rim at the communicating opening, the first membrane includes a first plate and an annular wall extending from a periphery of the first plate, the annular wall forms a stop ring extending outwardly from one end of the annular wall disposed away from the first plate, the first slit is formed on the first plate, the annular wall is inserted in the first tube and contacts the first tube, and the stop ring and the rim abuts each other for securement therebetween;
   wherein the first tube includes two vents opposite to each other, the annular wall includes two through holes opposite to each other, the second membrane includes a second plate and two wings extending from two sides of the second plate, a protrusion extends from a distal end of each of the wings, the second slit is formed on the second plate, the second plate and the first plate overlap and contact each other, the wings pass through the respective through holes and the respective vents for securement, and the protrusion and the first tube engage each other.

2. The medical joint of claim 1, wherein the first slit and the second slit intersect each other.

3. The medical joint of claim 2, wherein an included angle is formed between the first slit and the second slit, and the included angle ranges from 30 to 150 degrees.

4. The medical joint of claim 2, wherein an included angle is formed between the first slit and the second slit, and the included angle is 90 degrees.

5. The medical joint of claim 1, further comprising a first rotatable tube and a second rotatable tube, the first rotatable tube being connected to the first junction and rotatable with respect to the first tube, the second rotatable tube being connected to the second junction and rotatable with respect to the second tube.

6. The medical joint of claim 5, wherein a first engagement ring extends from the interior of the first tube, a first annular recess is formed on the exterior of the first rotatable tube, the first rotatable tube is inserted in the first tube via the first junction, and the first engagement ring is engaged with the first annular recess.

7. The medical joint of claim 5, wherein a second annular recess is formed on the exterior of the second tube, a first engagement ring extends from the interior of the second rotatable tube, one end of the second rotatable tube encloses the second junction of the second tube, and the first engagement ring is engaged with the second annular recess.

8. The medical joint of claim 1, wherein the connection tube is a Y-shaped tube or a T-shaped tube.

9. The medical joint of claim 1, wherein the first plate includes a plurality of protruding points extending therefrom, the second plate is disposed with a plurality of trenches, and the protruding points are engaged with the trenches respectively.

10. The medical joint of claim 1, wherein the first plate and the second plate are each a convex plate protruding in a direction away from the communicating opening.

11. The medical joint of claim 1, wherein the first membrane and the second membrane consist of plastic or rubber.

12. A check valve module, for use with a connection tube, the connection tube including a communicating opening, the check valve module comprising:
    a first membrane assembled to the communicating opening to seal the communicating opening, the first membrane including a first slit; and
    a second membrane, the first membrane and the second membrane being disposed overlappingly, the second membrane including a second slit,
    wherein the connection tube is formed with a rim at the communicating opening, the first membrane includes a first plate and an annular wall extending from a periphery of the first plate, the annular wall forms a stop ring extending outwardly from one end of the annular wall disposed away from the first plate, the first slit is formed on the first plate, the annular wall is inserted in the first tube and contacts the first tube, and the stop ring and the rim abuts each other for securement therebetween;
    wherein the connection tube includes two vents opposite to each other, the annular wall includes two through holes opposite to each other, the second membrane includes a second plate and two wings extending from two sides of the second plate, a protrusion extends from a distal end of each of the wings, the second slit is formed on the second plate, the second plate and the first plate overlap and contact each other, the wings pass through the respective through holes and the respective vents for securement, and the protrusion and the connection tube engage each other.

13. The check valve module of claim 12, wherein the first slit and the second slit intersect each other.

14. The check valve module of claim 13, wherein an included angle is formed between the first slit and the second slit, and the included angle ranges from 30 to 150 degrees.

15. The check valve module of claim 13, wherein an included angle is formed between the first slit and the second slit, and the included angle is 90 degrees.

16. The check valve module of claim 12, wherein the first plate includes a plurality of protruding points extending therefrom, the second plate is disposed with a plurality of trenches, and the protruding points are engaged with the trenches respectively.

17. The check valve module of claim 12, wherein the first plate and the second plate are each a convex plate protruding in a direction away from the communicating opening.

18. The check valve module of claim 12, wherein the first membrane and the second membrane consist of plastic or rubber.

\* \* \* \* \*